United States Patent [19]

Cohen et al.

[11] Patent Number: 5,093,258
[45] Date of Patent: Mar. 3, 1992

[54] RECOMBINANT FOWLPOX VIRUS AND RECOMBINATION VECTOR

[75] Inventors: Lawrence K. Cohen, Brighton; Dennis L. Panicali, Acton, both of Mass.

[73] Assignee: Therion Biologics Corporation, Cambridge, Mass.

[21] Appl. No.: 237,285

[22] Filed: Aug. 26, 1988

[51] Int. Cl.$^5$ .................. C12N 7/01; C12N 15/86; C12N 15/39; A61K 39/295
[52] U.S. Cl. ............... 435/235.1; 43.5/320.1; 43.5/122.3; 424/89; 935/6; 935/32; 935/65
[58] Field of Search ............ 435/235, 172.1, 172.3, 435/69.1, 69.3, 70.1, 320, 22, 23, 32, 34, 57, 63, 65

[56] References Cited

U.S. PATENT DOCUMENTS 4,603,112  7/1986  Paoletti et al. .............. 435/235

FOREIGN PATENT DOCUMENTS

| EP0284416 | 1/1988 | European Pat. Off. |
| EP0308220 | 3/1989 | European Pat. Off. |
| EP0314569 | 5/1989 | European Pat. Off. |
| 0338807 | 10/1989 | European Pat. Off. |
| 87/00323 | 3/1988 | PCT Int'l Appl. |
| 8802022 | 3/1988 | PCT Int'l Appl. |
| WO86/00528 | 1/1986 | World Int. Prop. O. |
| WO 8903429 | 4/1989 | World Int. Prop. O. |
| WO 8903879 | 5/1989 | World Int. Prop. O. |
| WO89/07644 | 8/1989 | World Int. Prop. O. |
| WO89/12684 | 12/1989 | World Int. Prop. O. |

OTHER PUBLICATIONS

Panicali et al., (1986), Gene, 47:193–199.
Mackett et al., (1986), J. Gen. Virol., 67:2067–2082.
Taylor, J. et al., Vaccine, 6:497–503, (1988).
Taylor, J. et al., Vaccine, 6:504–508 (1988).
Boyle, D. B. and B. E. H. Coupar, J. Gen. Virol., 67:1591–1600 (1986).
Boyle, D. B. et al., Virology 156:355–365 (1987).
Tomley, F. et al., J. Gen. Virol., 69:1025–1040 (1988).
Binns, M. M. et al., Virology, 170:288–291 (1989).
International Search Report for the corresponding PCT Application.
Taylor, J. et al., Technological Advances in Vaccine Development, (1988), L. Lasky (Ed.), Alan R. Liss, Inc., New York, pp. 321–334.
Binns, M. M. et al., Israelian J. Vet. Med., 42:124–127 (1986).
Boyle, B. B. and B. E. H. Coupar (1988), Virus Res., 10:343–356.

Primary Examiner—Richard A. Schwartz
Assistant Examiner—Mary E. Mosher
Attorney, Agent, or Firm—Sewall P. Bronstein; Ronald I. Eisenstein

[57] ABSTRACT

Recombinant fowlpox virus (FPV) capable of expressing immunogenic proteins of fowl pathogens are described. The FPV express DNA of the pathogen under the direction of FPV promoters. The recombinant FPV provide live vaccines for poultry and other animals.

20 Claims, 8 Drawing Sheets

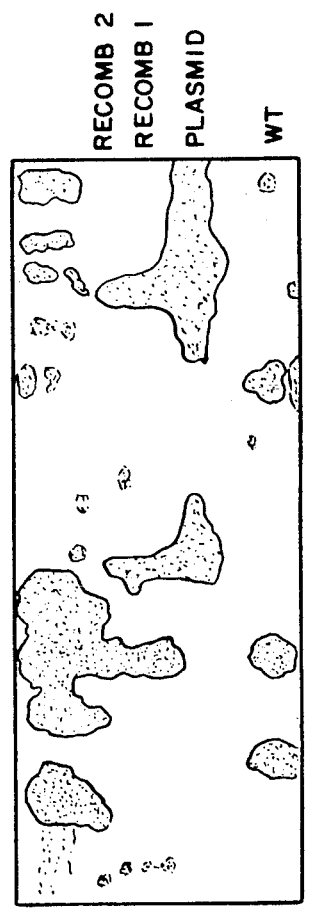
GENE REPLACEMENT
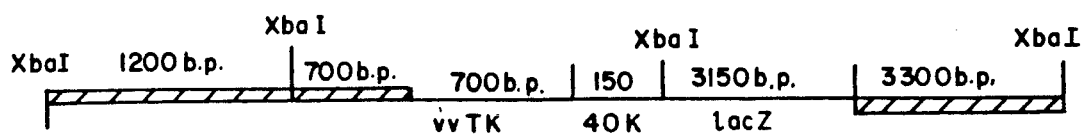
W.T. FPTK
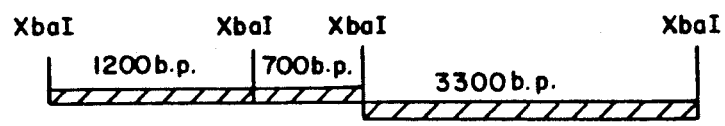
FIG. 3B

GGATCCCCCATCG ATG   GGG AAT TCA
‾‾BamHI‾‾   ‾ClaI‾       ‾EcoRI‾

G GAT CCC GTC GTT TTA CAA
 ‾BamHI‾

Sequences of $C_1$ Promoter:

```
  1 GATCATTATT TAACGTAAAC TAAATGGAAA AGCTATTTAC AGGTACATAC GGTGTTTTCT
 61 GGAATCAAAT GATTCTGATT TTGAGGATTT TATCAATACA ATAATGACAG TGCTAACTGG
121 TAAAAAAGAA AGCAAACAAT TATCATGGCT AACAATTTTT ATTATATTTG TAGTATGCAT
181 AGTGGTCTTT ACGTTCTTT ATTTAAAGTT AATGTGTTAA GATTAAATGG AGCAATTTGA
241 TC
```

Sequence of $C_2$ Promoter:

```
  1 GATCTGAATA TATGATACCC AGTAATAAAG CATGGAAAGT GATCCTTCCT CTAAAGTATA
 61 ACTATGATC
```

Sequence of Modified $C_1$ Promoters:

The sequence of the modified promoters is identical to $C_1$ with the following exceptions –

```
           220bp    ┌initiation codon of C₁-lacZ fusion protein
            ↓       ┌─┐
C₁:     AGATTAAATGGAGCAATTTGATC
                 ↓       ↓
2137:   AGATTAAATAGAGCAATTGGATC
                 ↓       ↓
2138:   AGATTAAATGGAGTAATTGGATC
                      └┬─┘
                       └→ a termination codon
                          in frame with
                          native ATG.
```

FIG. 5

RECOMBINANT FOWLPOX VIRUS AND RECOMBINATION VECTOR

BACKGROUND

Fowlpox virus (FPV) is the archetypal member of the avian poxviruses and the causative agent of pox in poultry (Woodruff, A.M., and E.W. Goodpasture (1931) *Am. J. Pathol.* 7:209-222; Woodruff, C.E., and E.W. Goodpasture (1929) *Am. J. pathol.* 5:1-10; Woodruff, C.E., and E.W. Goodpasture (1930) *Am. J. Pathol.* 6:713-720). The virus particle is brick-shaped with dimensions of 260×350 nm and possesses the typical poxvirus structure. An outer membrane system encloses the lateral bodies and the biconcave core containing the viral genome which has been estimated at 200-240×10⁶ daltons (Gafford, L.G. and C.C. Randall (1967) *J. Mol. Biol.* 26:303-310).

Pox of birds is prevalent world-wide but is not considered a public health problem since the host-range of the avian poxviruses is limited to birds and excludes mammals (Tripathy, D.N. and G.H. Cunningham (1984) Avian Pox, Chapter 23, pp. 524-534, in *Diseases of Poultry*, 8th ed. M.S. Hofstad ed.). Chickens of all ages are susceptible to the disease and while mortality is usually low, infection causes a temporary decrease in egg production and a significant reduction in the growth rate of young birds. FPV infection most often occurs by mechanical transmission to injured or lacerated skin although the virus can also be transmitted by mosquitoes (DaMassa, A.J. (1966) *Avian Dis.* 10:57-66). After an incubation period of 4 to 10 days, the disease manifests itself as one or a combination of three forms: (1) cutaneous lesions of featherless areas; (2) dipthenic lesions of the mouth; and (3) coryzal lesions of nasal passages (Tripathy, D.N., and C.H. Cunningham (1984) Avian Pox, Chapter 23, pp. 524-534, in *Diseases of Poultry*, 8th ed. M.S. Hofstad ed.). In uncomplicated infections the disease lasts 3-4 weeks and results in life-long immunity in the bird, a result of both humoral and cell-mediated responses (Tripathy, D.N., and L.E. Hanson (1975) *Am. J. Vet. Res.* 36:541-544).

Attenuated strains of FPV are currently being used by the poultry industry as vaccines to control the incidence of pox in chickens and turkeys. The live viral vaccine, which results in life-long immunity, is prepared on the chorioallantoic membrane of the chicken embryo or from chicken embryo fibroblast cell cultures. Vaccinations are administered to chicks as young as one day old either orally or by pricking the web-wing (Tripathy, D.N., and C.H. Cunningham (1984) Avian Pox, Chapter 23, pp. 524-534, in *Diseases of Poultry*, 8th ed. M.S. Hofstad ed.; Mayr, A., and K. Danner (1976) *Develop. biol. Standasr.* 33:249-259). The FPV vaccine has been used in combination with a vaccine for Marek's Disease Virus to protect against both diseases with a single innoculation (Siccardi, F.J. (1975) *Avian Dis.* 19:362-365).

Laboratory analyses of FPV have concentrated on the characterization of the growth of the virus in birds, the chorioallantoic membrane (CAM) of developing embryos, and tissue culture cells. Replication in the dermal or follicular epithelium of birds is similar to that on the CAM (Tripathy, D.N., and C.H. Cunningham (1984) Avian Pox, Chapter 23, pp. 524-534, in *Diseases of Poultry*, 8th ed. M.S. Hofstad ed.). After adsorption, penetration and uncoating of the virus, a host response consisting of hyperplasia and the replication of cellular DNA occurs for the first 72 hours and generally results in a 2.5 fold increase in the number of cells (Cheevers, W.P., and C.C. Randall (1968) *Proc. Soc. Exp. Biol. Med.* 127:401-405; Cheevers, W.P., D.J. O'Callaghan, and C.C. Randall (1968) *J. Virol.* 2:421-429). Viral DNA replication which is preceded by early protein synthesis occurs primarily between 60 and 96 hours post-infection and is followed by the synthesis of late proteins. The assembly of infectious virions occurs between 72 and 96 hours (Cheevers, W.P., and C.C. Randall (1968) *Proc. Soc. Exp. Biol. Med.* 127:401-405; Cheevers, W.P., D.J. O'Callaghan, and C.C. Randall (1968) *J. Virol.* 2:421-429).

The growth of FPV on tissue culture cells has been achieved on chicken embryo fibroblast cells, duck embryo fibroblast cells, and chicken embryo dermal cells (Gafford, L.G., and C.C. Randall (1976) *Virology* 33:112-120; Baxendale, W. (1971) *Vet. Rec.* 88:5-10; El-Zein, A., S. Nehme, V. Ghoraib, S. Hasbani, and B. Toth (1974) *Avian Dis.* 18:495-506). In each case, the viral cycle is similar and appears to be quicker than that defined in birds. In the CED cells DNA replication commences between 12 and 16 hours, and infectious virus particles first appear at 16 hours and continue to increase in number until 48 hours post-infection (Prideaux, C.T., and D.B. Boyle (1987) *Arch. Virol.* 96:185-199).

Investigations of the organization of the FPV genome have recently been reported by a number of laboratories. The thymidine kinase gene was identified by complementation of a thymidine kinase negative vaccinia virus, and the DNA sequence of this gene has been determined (Boyle, D.B., and B.H. Coupar (1986) *J. Gen. Virol.* 67:1591-1600; Boyle, D.B., B.H. Coupar, A.J. Gibbs, L.J. Seigman, and G.W. Both (1987) *Virology* 156:355-365). Importantly, this study demonstrated the functional cross-reactivity of FPV and vaccinia virus promoters. The FPV DNA polymerase gene was identified by amino acid homology to the vaccinia virus polymerase, and the DNA sequence of this gene was also reported (Binns, M.M., L. Stenzler, F.M. Tomley, J. Cambell, and M.E.G. Boursnell (1987) *Nucleic Acid Research* 16:6563-6573). Twenty-one polypeptides associated with the FPV infectious cycle have been detected by metabolic labeling of infected chicken dermal cells, and a 3.1 kb fragment of the FPV genome which demonstrates nucleic acid homology with the vaccinia virus Hind III J fragment has been identified (Prideaux, C.T., and D.B. Boyle (1987) *Arch. Virol.* 96:185-199; Drillien, R., Spehner, D., Villeval, D., and J.-P. LeCocq (1987) *Virology* 160:203-209).

Vaccinia virus, the archetypal member of the orthopox viruses, was employed as a vaccine for the successful worldwide erradication of smallpox. The success of the program is attributable in part to: (1) the high levels of both cellular and humoral immunity achieved in response to infection with vaccinia virus; (2) the stability of the virus; (3) the ease of administration of the vaccine; and (4) the relative safety of the innoculation.

Paoletti et al. have developed a technique known as in vivo recombination (IVR) which allows the insertion by site-specific recombination of foreign DNA into the vaccinia virus genome (U.S. Pat. No. 4,603,112), and has led to the use of vaccinia virus as a eukaryotic expression vector for creating live recombinant vaccines. A number of recombinant vaccinia virus have been created expressing either single or multiple genes encoding specific foreign viral antigens and upon vaccination have been shown to protect against challenge with the correlate pathogens.

Recently, Boyle, D. et al. have disclosed recombinant FPV containing foreign DNA within a nonessential region of the viral genome. International Patent Application PCT/AU87/00323. Vaccinia virus promoters are used to express the DNA in FPV.

SUMMARY OF THE INVENTION

This invention pertains to recombinant FPV which contain and express foreign DNA under the direction of a FPV promoter, to methods of producing the recombinant FPV and to the use of recombinant FPV for live viral vaccines.

Recombinant FPV capable of expressing foreign antigens are produced by integrating into the fowlpox viral genome a gene or genes encoding a foreign antigen(s). This foreign DNA sequence is inserted into a region of the FPV genome which is nonessential for replication of the pox virus. The foreign DNA is inserted into the genome in association with a FPV promoter to direct the expression of the foreign DNA.

The foreign DNA sequence is integrated into the FPV genome by an in vivo recombination event between an intermediate DNA vector carrying the foreign DNA sequence and the FPV genome. The intermediate DNA vector contains the foreign DNA sequence linked to a fowlpox viral promoter located between DNA sequences homologous to a region of the FPV genome which is nonessential for replication of FPV. Thus, the vector comprises:

a. a prokaryotic origin of replication;
b. one or more FPV promoters;
c. one or more DNA sequences encoding antigens, each DNA sequence being under the direction of a separate FPV promoter; and
d. DNA sequences of the FPV into which the gene encoding the antigen is to be integrated, the DNA sequences flanking the promoter and structural gene at both the 5' and 3' ends, the DNA sequence being homologous to the region of the FPV genome where the promoter(s) and foreign DNA sequence(s) are to be inserted.

In preferred form, the DNA vector for recombination with FPV also contains a gene which encodes a selectable marker which permits selection of viral recombinants containing the inserted foreign DNA. Thus, the vector will contain these additional elements located between the flanking FPV sequences:

e. a second pox viral promoter (preferably, a FPV promoter); and
f. a gene encoding a selectable marker, the gene being under the direction of the second pox viral promoter.

Recombination of the DNA vector with FPV is achieved in an appropriate eukaryotic host cell. Appropriate host cells for in vivo recombination are eukaryotic cells which are 1) transfectable by the DNA vector and 2) infectable by FPV. The host cell is infected with the FPV and then transfected with the DNA vector. Virus is allowed to replicate in the host cell and recombination occurs in vivo resulting in insertion of the foreign DNA into the FPV genome. The recombinant viral progeny is isolated away from the wild type virus. When a selectable marker has been co-integrated with the foreign DNA sequence, expression of the selectable marker provides a basis for selection of recombinant virus containing integrated foreign DNA. Other methods of selection include detection of integrated DNA by hybridization with homologous DNA probes or selection for absence of the product of the viral gene into which the DNA vector has been inserted.

The recombinant virus is a virus which expresses in tissue culture and in an inoculated host the foreign antigen of interest. The virally-expressed antigen will trigger cell-mediated and humoral immunity against the virus from which the antigen is derived.

There are a number of advantages to creating a recombinant FPV expressing foreign genes for use as live vaccines in fowl and perhaps other animals. Vaccination with a live virus would stimulate cell-mediated and humoral immunity. The proteins that are expressed are expected to be appropriately modified, and if the required signals are present, they may also be localized to the proper regions of the cell or cellular membrane (Stephens et al., *EMBO J*, 5:237 (1986)). In contrast to subunit vaccines, live virus vaccines stimulate both cell-mediated and humoral immunity. Additionally, a single FPV isolate could serve as a polyvalent vaccine against one or more pathogens as has been demonstrated in vaccinia virus (Perkus et al., *Science*, 229:981 (1985)). FPV vaccines can be manufactured inexpensively. The vaccines can also be administered relatively simply. Finally, a recombinant vaccine utilizing FPV would avoid the problems associated with vaccinating with live attenuated or killed pathogens: these pathogens may not be properly killed or can revert into virulent forms.

BRIEF DESCRIPTION OF THE FIGURES

FIG. 3a and 3b show hybridization analyses of DNA derived from recombinant FPV with insertions at two different sites.

FIG. 5 shows the DNA sequence of FPV promoters $C_1$ and $C_2$ and the DNA sequence of two modified $C_1$ promoters.

DETAILED DISCLOSURE OF THE INVENTION

Figure 1A:
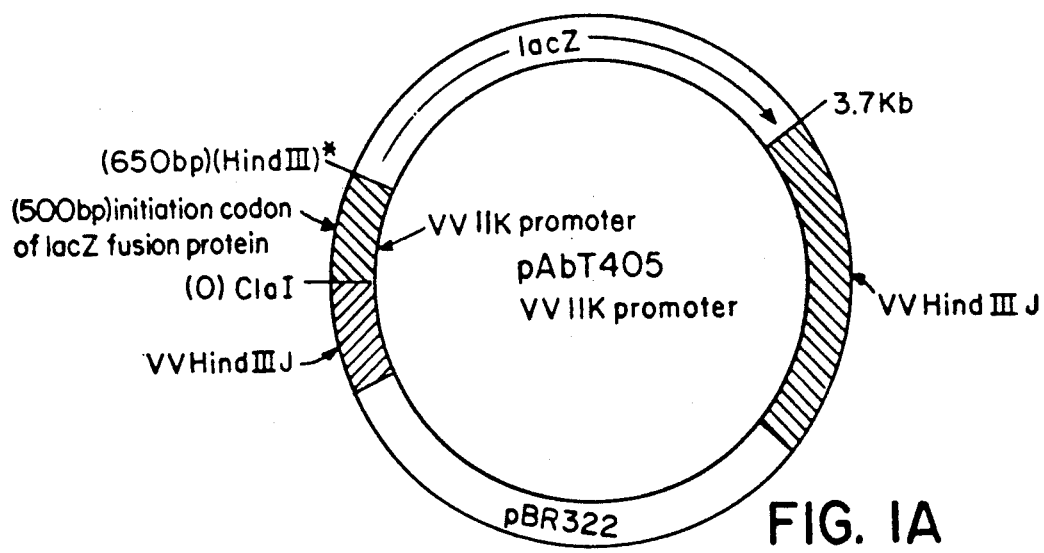
FIG. 1A-C shows two plasmids designated, pAbT 405 and pAbT 4523, containing vaccinia virus promoters and one plasmid designated, pAbT 2102, containing an FPV promoter directly upstream of the lacZ from *E. coli*.

1. Genes for Integration Into Pox Virus

Foreign genes for integration into the genome of a FPV in expressible form can be obtained by any conventional technique for isolating a desired gene. The genes can be derived from any organism, including bacteria, viruses or other microorganisms, for which a FPV-based live vaccine is desired. These genes will be derived from pathogens which are important to the poultry industry and includes those pathogens for which vaccines of variable efficacy already exist, namely; infectious bronchitis virus, infectious bursal disease virus, reovirus, Marek's disease virus, Newcastle disease virus, laryngo-tracheitis virus, and avian encephalomyelitis virus. The genes will also be derived from poultry pathogens for which no vaccines currently exist despite the need to control their spread. This list includes: *Eimeria* species which cause *coccidiosis salmonella gallinarum, Salmonella pullorum, Salmonella typhimurium, Staphylococcus auereus, Aspergillus flavus, Escherichia coli, Mycoplasma gallisepticum, Mycoplasma gallinarum, Mycoplasma synoviae*, RNA lymphoid leukosis virus, avian influenza, and hemorrhagic enteritis virus.

For purposes of a vaccine, genes of interest are those which encode immunogenic proteins of a pathogenic organism. In many cases, these are protein components of surface structures such as the bacterial cell wall or viral envelope. In appropriate instances, immunogenic fragments or subunits of the proteins may be used.

For organisms which contain a DNA genome, the genes encoding an antigen of interest are isolated from the genomic DNA; for organisms with RNA genomes, the desired gene may be isolated from cDNA copies of the genome. If restriction maps of the genome are available, strategies can be designed for cleaving genomic DNA by restriction endonuclease digestion to yield DNA fragments that contain the gene of interest. In some cases, desired genes may have been previously cloned and thus, the genes can be obtained from the available clones. Alternatively, if the DNA sequence of the gene is known, the gene can be synthesized by any of the conventional techniques for synthesis of deoxyribonucleic acids (e.g., the phosphate or phosphite triester techniques).

Genes encoding an antigen of interest can be amplified by cloning the gene into a bacterial host. For this purpose, various prokaryotic cloning vectors can be used. Examples are plasmids pBR322 and pEMBL.

The genes encoding the antigen of interest can be prepared for insertion into the DNA vectors designed for recombination with FPV by standard techniques. In general, the cloned genes can be excised from the prokaryotic cloning vector by restriction enzyme digestion. In most cases, the excised fragment will contain the entire coding region of the gene. The DNA fragment carrying the cloned gene can be modified as needed, for example, to make the ends of the fragment compatible with the insertion sites of the DNA vectors used for recombination with FPV, then purified prior to insertion into these vectors at restriction endonuclease cleavage sites (cloning sites) as described below.

2. DNA Vectors for Recombination With FPV

According to the method of this invention foreign genes which encode immunogenic proteins are inserted into the genome of FPV so as to allow them to be expressed by the FPV along with the expression of the normal complement of FPV proteins (except for the FPV protein encoded by the gene into which the foreign DNA is inserted). This is accomplished by first constructing a DNA vector for recombination with FPV which contains the foreign gene or genes of interest flanked by FPV sequences. The flanking FPV sequences can be derived from any FPV DNA region nonessential for replication; these allow the vector to recombine with the virus in vivo at a specific region in the viral genome. This recombination results in integration of the foreign DNA into the genome to produce a recombinant FPV containing the foreign gene or genes.

Preferred DNA vectors for integration of a foreign gene in expressible form into the FPV genome contain the following elements:
  a. a pox viral promoter linked to:
  b. a DNA sequence containing a multiple cloning site for insertion of foreign DNA;
  c. DNA sequences flanking the construct of elements a and b, the flanking sequences being homologous to a region of the FPV genome into which elements a. and b. are to be inserted;
  d a replicon for vector replication in a prokaryotic host; and
  e. a gene encoding a selectable marker or indicator for selection of the vector in transformed prokaryotic hosts.

The multiple cloning site comprises recognition sites for several restriction enzymes which allow different modes of insertion of foreign DNA. An example sequence containing a multiple cloning site is: GGATCCCCGGGTACCGAGCTCGAATTC, which contains the recognition sequences and cleavage sites for the restriction endonuclease enzymes BamHI, SmaI, KpnI, SacI and EcoRI. Sequences containing additional or different recognition sites can be used. The cloning site is located adjacent to and downstream of a pox viral promoter such that an inserted gene can be placed under transcriptional control of the promoter.

The pox viral promoter controls expression of the foreign gene inserted at the cloning site. The preferred promoter is derived from FPV but other pox viral promoters (e.g., vaccinia promoters) can also be used. FPV promoters are DNA sequences which direct messenger RNA synthesis from FPV genes during a virus infection. Such promoters can be isolated from the FPV genome or can be constructed by DNA synthesis techniques. Promoters vary in strength of activity and in time of expression during the FPV replication cycle; these parameters can be altered by mutation of the promoter sequence. Especially preferred are the FPV $C_1$ and $C_2$ promoters having the sequences shown in FIG. 5. Modified versions of the $C_1$ promoter such as those shown in FIG. 5 can also be used.

The sequences flanking the construct of elements a and b (the pox viral promoter and adjacent cloning site) are homologous to a region of the FPV genome which is not necessary for replication of the FPV. Thus, recombination and integration of foreign DNA will occur at this site and the inserted DNA will not abolish viral replication.

The preferred FPV region for recombination and insertion of foreign DNA is the BamHI J fragment of FPV. Recombination can be directed to the BglII site within this fragment. This can be accomplished by employing, as 5' flanking sequences in the vector, DNA homologous to the region of the BamHI J fragment which is 5' of the BglII site and, as 3' flanking sequences, DNA homologous to the region of the BamHI J fragment which is 3' of the BglII site.

The foreign DNA can also be inserted into FPV TK sequences. However, insertion within the FPV TK gene has been shown to interfere with FPV replication and consequently, a compensatory pox viral TK gene (e.g., the vaccinia virus TK gene) must be inserted into the FPV genome along with the foreign DNA to provide a functional TK gene. Thus, DNA vectors for inserting foreign DNA into the FPV TK gene contain a pox viral TK gene and gene regulatory sequences within FPV TK flanking sequences.

The replicon for replication in a prokaryotic host and the gene encoding the selectable indicator or marker allow the vector to be selected and amplified in a prokaryotic host such as E. coli to provide ample quantities of the vector DNA for eventual transfection of eukaryotic host cells for recombination. The replicon can be obtained from any conventional prokaryotic vector such as pBR322 or pEMBL. The selectable marker can be a gene conferring antibiotic resistance (e.g. ampicillin, chloranyshenicol, kanamycin or tetracycline resistance).

Preferred vectors contain genetic elements which permit positive selection or identification of recombinant FPV i.e., those viruses which have recombined with the vector and, as a result, have acquired the foreign DNA sequences. These elements comprise a gene encoding a selectable marker or indicator and a pox viral promoter which controls expression of the gene in the recombinant virus. The promoter and marker or indicator gene are located between the flanking FPV sequences so that the elements which allow for selection or identification and the foreign gene of interest are cointegrated into the FPV genome. Recombinant FPV can then be selected based upon expression of the marker or indicator.

A preferred gene for identification is the *E. coli* lacZ gene which encodes the enzyme B-galactosidase. Methods of identification based upon expression of this enzyme are discussed below. Selection methods include any drug resistance selection, for example, the selection that is provided by the gene encoding xanthine-quanine phosphoribosyl transferase, which confers resistance to mycophenolic acid of that encoding neomycin phosphotransferase, an enzyme which confers resistance to G418 (Franke et al., (1985) Mol. Cell, Biol. 5, 1918; Falkner, F.G. and B. Moss (1988) *J. Virol.* 62:1849-1854.)

Accordingly, a vector for recombination with FPV can contain:

a. an FPV promoter (e.g. the $C_1$ or $C_2$ FPV promoters of FIG. 5 or modified versions of these promoters);
b. a multiple closing site adjacent to the promoter;
c. a second pox viral promoter (preferably derived from FPV);
d. a gene encoding an identifiable marker (e.g. the *E. coli* lacZ gene) under the control of element c.;
e. DNA sequences homologous to a region of the FPV genome into which elements a.-d. are to be inserted, the DNA sequences flanking the construct of elements a-d;
f. a replicon for replication in a bacterial host; and
g. a gene encoding a selectable marker under control of a prokaryotic promoter for selection of the vector in a prokaryotic host.

Two or more foreign DNA sequences can be inserted into FPV by a single in vivo recombination event. For this purpose, vectors are provided for introduction of two or more foreign DNA sequences into FPV. These vectors can be employed to produce recombinant FPV which express two or more different antigenic proteins to provide multivalent vaccines. The proteins can be derived from one or more organisms. Vectors for introduction of multiple foreign DNA sequences into FPV contain the elements as described above for a monovalent vector and one or more additional pox viral promoters (preferably FPV promoters), each followed by a multiple cloning site for insertion of one or more additional genes encoding immunogenic proteins of one or more organisms. The additional promoter(s) and multiple cloning site(s) are located between the flanking FPV sequences which direct recombination into the FPV genome. A vector for introduction of two or more foreign DNA sequences into a FPV can comprise any combination of two, three or more of the various FPV promoters, each followed by a multiple cloning site for insertion of a different gene of interest. For example, a divalent vector can contain:

a. a first FPV promoter followed by a multiple cloning site appropriately situated so that any inserted DNA sequence is controlled by the promoter;
b. a second FPV promoter and adjacent cloning site; and
c. a third FPV promoter linked to a foreign DNA sequence encoding a selectable marker or indicator.

This construct is flanked by sequences of FPV which direct recombination. The first, second, and third promoters must be different promoters. There are several advantages to using different promoters in one vector. Different promoters may have varying strengths of activity and different times of expression during the viral life cycle. Separate promoters are also required to ensure the stability of the ensuing recombinant FPV. It has recently been demonstrated that tandem repeats of identical nucleic acid sequences are unstable in pox virus genomes, and are removed through homologous recombination during replication of the viral genomes (Ball, L.A. (1987) *J. Virol.* 61:1788-1795; and Spyropoulos, D.D., B.E. Roberts, D.L. Panicali, and L.K. Cohen (1988) *J. Virol.* 62:1046-1054). The parameters for optimal expression of different antigens may vary with each antigen and therefore different promoters may be optimal.

Because of the convenient multiple cloning sites, any isolatable gene(s) can be easily inserted into these monovalent and divalent in vivo recombination vectors.

4. In Vivo Recombination

The intermediate DNA vectors containing the DNA sequence of interest (and the marker or indicator gene) flanked by appropriate FPV sequences will undergo recombination with FPV which results in integration of the flanked genes into the FPV viral genome. This recombination will occur in a eukaryotic host cell. Appropriate host cells for recombination are cells which are 1) infectable by FPV and 2) transfectable by the DNA vector. Examples of such cells are chick embryo fibroblast (CEF), and chick embryo dermal (CED) cells.

The cells are first infected with FPV and then transfected with the intermediate DNA vector. Viral infection is accomplished by standard techniques for infection of eukaryotic cells with FPV. See e.g., Paoletti et al., supra. The cells can be transfected with the intermediate DNA vector by any of the conventional techniques of transfection. These include the techniques of calcium phosphate precipitation, DEAE dextran, electroporation and protoplast fusion. The preferred technique is the calcium phosphate precipitation technique.

After infection and subsequent transfection, the cells are incubated under standard conditions and virus is allowed to replicate during which time in vivo recombination occurs between the homologous FPV sequences in the intermediate vector and FPV sequences in the genome.

Recombinant viral progeny are then selected by any of several techniques. The presence of integrated foreign DNA can be detected by hybridization with a labeled DNA probe specific for the inserted DNA. Preferred techniques for selection, however, are based upon co-integration of a gene encoding a marker or indicator gene along with the gene of interest, as described above. A preferred indicator gene is the *E. coli* lacZ gene which encodes the enzyme beta-galactosidase. Selection of recombinant FPV expressing beta-galactosidase can be done by employing a chromogenic substrate for the enzyme. For example, recombinant viruses are detected as blue plaques in the presence of the substrate 5-bromo-4-chloro-3-indolyl-B-D-galactoside or other halogenated-indolyl-B-D-galactosides (e.g., BluoGal ™).

5. Vaccines

Live recombinant FPV expressing immunogenic proteins from one or more pathogens can be used to vaccinate poultry susceptible to these pathogens. Recombinant FPV may also be useful to vaccinate animals other than poultry. These vaccines may be administered intradermally, or by other routes appropriate to the recombinant virus used and the disease for which protection is desired. These may include among others, intra-muscular, subcutaneous and oral routes. Vaccination with live recombinant FPV is followed by replication of the virus within the host. During replication, the foreign DNA sequence(s) is expressed along with the normal complement of FPV genes. If the foreign DNA sequence encodes an antigen, the host will mount an immunological response, both humoral and cell-mediated, to the foreign antigen as well as to FPV itself. If the foreign antigen can stimulate a protective immunological response, then the host animal will be immune to infection by the corresponding pathogenic agent.

Live recombinant FPV containing and expressing one or more of the genes encoding immunogenic proteins of pathogenic agents can serve as monovalent and divalent vaccines.

An additional advantage of utilizing recombinant FPV as live vaccines is that they express only selected antigens, preferably only those antigens sufficient to elicit a protective immune response to the corresponding pathogen. It is therefore possible to differentiate between host animals which have been vaccinated with the recombinant FPV and those which have been infected with the authentic, virulent, disease-causing agent.

The vaccinated host will develop antibodies only to the FPV and to the selected foreign antigen(s). By contrast, the actively infected host will generate a full complement of antibodies directed toward the pathogenic agent, including antibodies directed to specific antigens not present in the recombinant FPV. The presence of these additional antibodies, which can be detected using appropriate immunological tests (e.g., ELISA), is therefore diagnostic of a naturally occuring infection of the host with the pathogen.

The invention is illustrated by the following Exemplification.

EXEMPLIFICATION

Materials and Methods

1. Cells

Primary chicken embryo fibroblast (CEF) and chicken embryo dermal (CED) cells were prepared by published procedures (Rein, A., and H. Rubin (1968) *Exp. Cell Res.* 49:666; Silim, A., M.A.S.Y. El Azhary, and R.S. Roy (1982) *Avian Dis.* 26:182–185). The fibroblast cultures were maintained in Dulbecco's Modified Eagle Media (DME) supplemented with 10% calf serum (CS), and the dermal cells were maintained in Minimum Essential Media (MEM) containing 5% fetal calf serum (FCS). The fibroblast cultures were maintained for a maximum of 3 passages in tissue culture and the dermal cells for a maximum of 6 passages. All cells were grown at 37° C. and under 5% $CO_2$.

2. Virus Strains

A FPV vaccine strain obtained from Schering-Plough and designated for research purposes only, was employed exclusively in these studies. The strain was plaque purified twice on both CEF and CED monolayers before use.

3. Amplification and Purification of FPV

Viral stocks were prepared on CED monolayers by infection at a multiplicity of infection (moi) of 0.01 and replication was allowed to proceed for 5 days at 37° C. and 5% $CO_2$. Infected cells were scraped directly into the culture media and virus was released by multiple cycles of freezing and thawing.

The amplification of single plaque isolates was conducted by infection of $2\times10^6$ cells in a confluent monolayer with one-half of the plaque pick. After five days of replication, the progeny virus were harvested, released by multiple cycles of freezing and thawing, and one-third of that material was used to inoculate $1\times10^7$ cells. Amplification was again allowed to proceed for five days, and the resulting virus was harvested by scraping the cells into the culture media, and released by multiple cycles of freezing and thawing. A viral stock prepared in this fashion results in a stock containing approximately $1\times10^8$ pfu.

Partially purified virus was prepared, when necessary, by centrifugation by a procedure developed for the purification of vaccinia virus (Joklik, W.K. (1962) *Virology* 13:9–18).

4. Plaque Assay of FPV

Plaque formation of FPV was accomplished on monolayers of CED cells which were seeded at a density of $2\times10^6$ cells per 60 mm tissue culture dish. Viral suspensions were allowed to adsorb to the cells in 1.0 ml of MEM containing 2% FCS for 90 minutes, and were removed by aspiration and replaced with 5.0 mls of 0.6% agarose containing DME and 2% CS. The plaques formed at 37° C. and 5% $CO_2$ were generally visible after 48 hours, and were stained for 12 to 48 hours with an additional agarose overlay containing 0.001% neutral red. The Beta-galactosidase activity following plaque formation was detected with an agarose overlay containing DME and 300 ug/ml of 5-bromo-4-chloro-3-indolyl-$\beta$-D-galactopyranoside (X-gal).

5. FPV-Based Transient Expression Assays

The FPV-based transient assay was based directly on the assays which have been developed for use with vaccinia virus (Panicali, D.L., A. Grzelecki, and C. Huang (1986) *Gene* 193–199; Cochran, M.A., M. Mackett, and B. Moss (1985) *Proc. Natl. Acad. Sci. USA* 82:19–23). Confluent monolayers of $2\times10^5$ CEF cells were infected with FPV at an moi of 1 for 60-90 minutes. After this, the inoculum was removed and replaced with growth medium. About 2.5 ug of a plasmid DNA containing a putative FPV promoter element directly upstream of the *E. coli* lacZ was precipitated from 62.5 ul of N-2-hydroxyethyl-piperazine-N'-2-ethanesulfonic acid (HEPES)-buffered saline (20 mM HEPES, 150 mM NaCl, 0.7 mM $Na_2HPO_4$, 5 mM KCl, and 6mM glucose [pH 7.0]) by the addition of 3.9 $\mu$l of 2 M $CaCl_2$ at room temperature for about 30 to 45 minutes. This precipitated DNA was added directly to the growth media 45 minutes after the removal of the viral inoculum. Viral replication and transient expression were allowed to proceed for approximately 24 hours, after which time the media and transfected DNA were removed and replaced with 1 mg/ml o-nitrophenyl-$\beta$-D-galactosidase (ONPG) in phosphate buffered saline (PBS, 2.7 mM KCl, 1.5 mM $KH_2PO_4$, 137 mM NaCl, and 8.1 mM $Na_2PO_4$). Incubation in the presence of the chromogenic indicator was conducted at 37° C. for times varying between 1 to 12 hours after which the production of nitrophenol was measured by absorbance at 420 nm.

6 Conditions for the Formation of Recombinant FPV

Confluent monolayers of $2 \times 10^6$ CEF cells in 60 mm tissue culture dishes were infected at an moi of 0.1 for about 60 to 90 minutes in MEM containing 2% FCS. Following adsorption of the virus, the inoculum was removed and replaced with 5.0 ml of growth medium. Twenty $\mu$g of plasmid DNA in 500 ul of HEPES-buffered saline was precipitated from the buffer by the addition of 31 $\mu$l of 2 M $CaCl_2$ at room temperature for 30 to 45 minutes. The precipitated plasmid DNA was added directly to the growth medium. Viral replication and recombination were allowed to proceed for an additional 72 hours. The viral progeny were harvested by scraping the CEF cells directly into the growth media, released by multiple cycles of freezing and thawing, and titered on confluent monolayers of CED cells.

7. Identification of Recombinant FPV Using A Single Cell Beta-Galactosidase Assay Monolayers consisting of $1 \times 10^6$ CED cells in 35 mm dishes were infected with recombinant FPV at an moi of 1.0 in MEM containing 2% FCS. After 60 to 90 minutes the FPV inoculum was removed and replaced with 3.0 ml of growth medium. Infection was allowed to proceed for an additional 24 hours. Growth media was removed, the monolayers washed 3 times in 3.0 ml of PBS, and the cells fixed in 0.5% glutaraldehyde in PBS for 5 to 15 minutes at room temperature. Following fixation, the glutaraldehyde was removed by three washes with PBS at room temperature for 3 to 5 minutes each. The cells were stained for beta-galactosidase activity at 37° C. for 2 to 6 hours with a solution of 1 mg/ml X-gal in 5 mM potassium ferrioyanide, 5 mM potassium ferrocyanide, and 1 mM $MgSO_4$ in PBS. Following staining, the cells were washed extensively with PBS and examined microscopically for the presence of stained cells. Cells which are stained blue are indicative of beta-galactosidase activity.

8. Preparation of Viral Genomic DNA

FPV genomic DNA was prepared by a method developed for vaccinia virus from $2.5 \times 10^7$ cells which had been infected 5 days previously with FPV at an moi of 0.1 (Esposito, J., R.C. Condit, and J. Obejeski (1981) *J. Virol. Methods* 2:175-179). The infected cells were scraped directly into the growth medium and were harvested by centrifugation at 3000 rpm for 10 minutes in a clinical centrifuge. The supernatant was discarded and the cell pellet washed 3 times by resuspension in 10 ml of PBS and recentrifuged. The final washed cell pellet was resuspended in 1.8 ml of 10 mM Tris-Cl (pH 7.8), 5 mM EDTA, and 10 mM KCl, and incubated on ice for about 10 minutes with intermittent vortexing. One $\mu$l of 2-mercaptoethanol and 200 $\mu$l of a solution of 10% triton X-100 were added and the cells were lysed for an additional 10 minutes on ice. Nuclei and large debris were removed by centrifugation at 2000 rpm for 10 minutes in a clinical centrifuge and the supernatant containing the partially purified virus was treated at 37° C. for one hour with 1 $\mu$l of 2-meroaptoethanol, 10 $\mu$l of a 20 mg/ml solution of proteinase K in $H_2O$, 40 $\mu$l of 5 M NaCl, and 100 $\mu$l of 10% SDS. The supernatant was then extracted twice with phenol/chloroform (1/1:v/v). The genomic DNA was then precipitated by the addition of one tenth the volume of 3M sodium acetate and 2 volumes of ethanol at −20° C. for about 30 minutes. The nucleic acid was collected by centrifugation at 12000 rpm for 10 minutes in a Sorvall SS-34 rotor, and, after drying, was resuspended in 40 ul of 10 mM Tris-cl (pH 8.0), 1 mM EDTA, and 1 $\mu$g/ml of RNase A.

9. Hybridization Analysis

Viral genomic DNA was digested with restriction endonuclease Bam HI for 4 hours and the resulting fragments were resolved on 1% agarose gels containing 40 mM Tris-acetate (pH 8.0), 2 mM EDTA. The fragments were transferred to nitrocellulose and analyzed by hybridization to the appropriate radio-labelled DNA by standard procedure (Maniatis, T., E.F. Fritsch, and J. Sambrook (1982) *Molecular Cloning*, A Laboratory Manual).

10. Construction of Plasmids

All manipulations, including plasmid isolation, restriction endonuclease digestion, agarose gel electrophoresis, fragment isolation, phosphatase treatment, use of linkers, ligation, and bacterial transformations were performed by standard published procedures (Maniatis, T., E.F. Fritsch, and J. Sambrook (1982) *Molecular Cloning*, A Laboratory Manual).

EXAMPLES

Example 1: Definition of Promoters Active During the FPV Infectious Cycle

The identification of pox viral DNA sequences able to control transcription in infected cells was accomplished through the use of a FPV-based transient expression assay developed for these purposes. In this system, DNA is transfected onto infected cells and, in the presence of the proper regulatory sequences, is expressed by the transcriptional apparatus of the infecting FPV. This system has been optimized for sensitivity with respect to cell type, infecting moi, the amount of exogenous DNA, the method for transfection, and time of infection, as well as incubation with the chromogenic indicator, ONPG (data not shown).

Figure 1B:
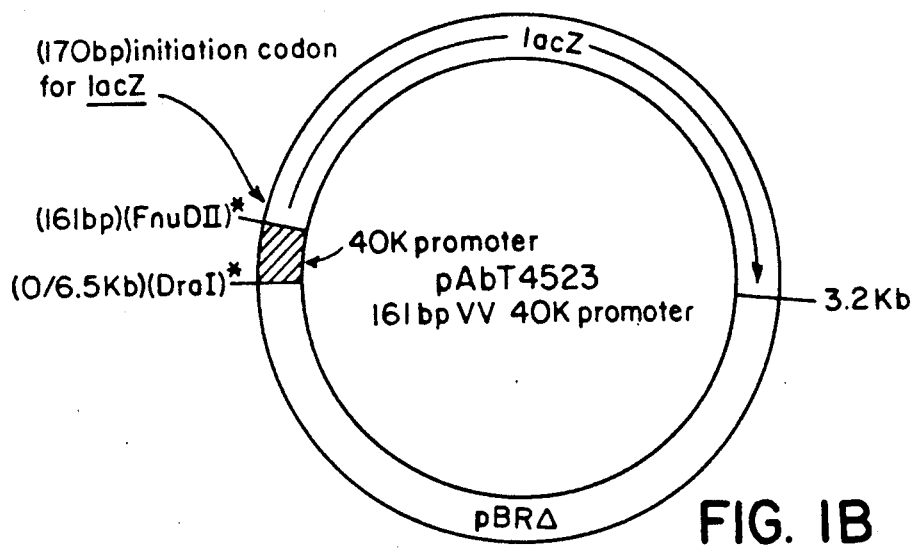
Figure 1C:
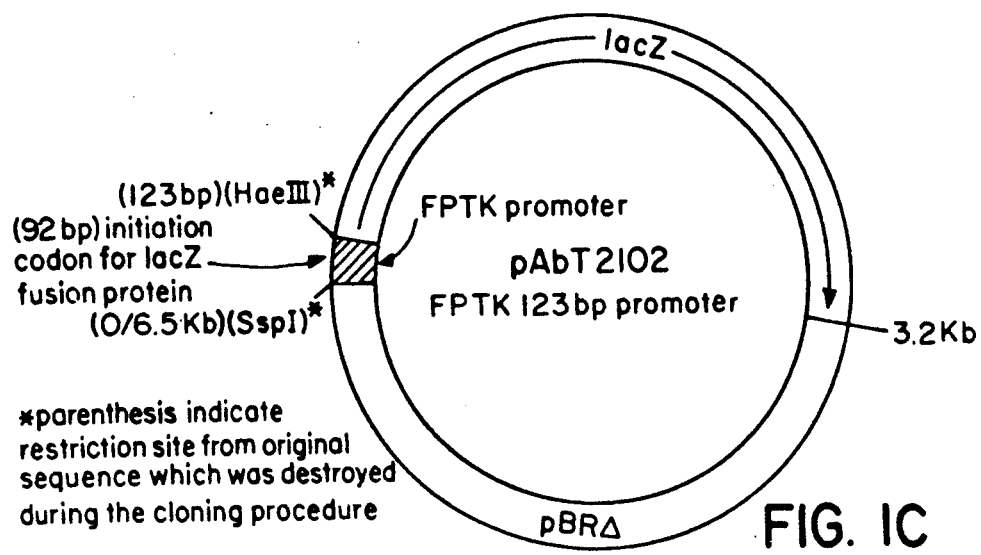

As shown in FIG. 1, two vaccinia virus promoters and a presumptive FPV promoter were placed directly upstream of lacZ to allow their activities to be measured during FPV infection.

Plasmid pAbT 405 contains the 650 bp Cla I to Hind III fragment from the right-hand end of the Hind III F fragment of the vaccinia virus genome. This segment contains the vaccinia virus promoter, translational start codon, and approximately 150 base pairs from the 5'-terminus of the gene which encodes an 11 Kd polypeptide expressed after DNA replication in the infectious cycle (Bertholet, C., Drillien, R. and R. Wittek (1985) *Proc. Natl. Acad. Sci. USA* 82:2096-2100).

Plasmid pABT 4523 contains the 161 bp Dra I to FnuD II fragment derived from the right-hand end of the Hind III H fragment of the vaccinia virus genome ligated to the lacZ derived from plasmid pDP 500 (Panicali, D.L., A. Grzelecki, and C. Huang (1986) *Gene* 193-199). This lacZ gene is complete, containing its own translational start and the resulting polypeptide is, therefore, not a fusion protein. This vaccinia virus promoter element, which controls the synthesis of a 40 Kd polypeptide, functions prior to, as well as following, viral DNA replication and is classified as a constitutive promoter (Rosel, J.L., P.L. Earl, J.P. Wier, and B. Moss (1986) *J. Virol.* 60:436-449).

Plasmid pAbT 2102 contains a 123 bp fragment derived from FPV genomic DNA which includes 92 bp preceding the translational start of the FPV thymidine kinase gene, the translational start codon and 29 bp of coding sequences which immediately follow (Boyle, D.B., B.H. Coupar, A.J. Gibbs, L.J. Seigman, and G.W. Both (1987) *Virology* 156:355-365). Based upon the location of promoters in other poxviruses, this DNA sequence was presumed to contain the FPV promoter element and was ligated to the lacZ gene derived from plasmid pDP 503(Panicali et al., 1986, Gene 47:193-199. The polypeptide synthesized from this construction would be a fusion of 10 amino acids derived from the FPV thymidine kinase to the beta-galactosidase polypeptide.

As shown in Table 1, each of these promoter-lacZ constructions produced measurable beta-galac-tosidase in the FPV-based transient expression assay, and the production of beta-galactosidase was dependent upon the appropriate plasmid. It is important to note that the assays of plasmids containing the two vaccinia virus derived promoters were read after 1.75 hr of incubation with the chromogenic substrate, while the assays containing the FPV derived promoter or no DNA were read after 9.0 hr of incubation. Clearly, each of these promoter elements are active during the FPV infectious cycle, and assuming that the measure of beta-galactosidase activity is directly proportional to promoter activity, can be ordered in decreasing activity as pAbT 4523 - pAbT 405 - pAbT 2102.

TABLE 1

DETECTION OF BETA-GALACTOSIDASE ACTIVITY IN A FPV-BASED TRANSIENT EXPRESSION ASSAY.

| PLASMID | Promoter Element | $A_{420}$ |
|---|---|---|
| pAbT 405 | vaccinia virus 11 K | .268* |
| pAbT 4523 | vaccinia virus 40 K | .490* |
| pAbT 2102 | fowl pox virus TK | .193 |
| none | | .082 |

Confluent monolayers of $2 \times 10^5$ CEF cells were infected and transfected as described in the Materials and Methods. $A_{420}$ was measured after 1.75 hour for those readings marked with an '*', and 9.0 hours for the remaining readings.

Example 2: Formation and Identification of Recombinant FPV

The vaccinia virus promoter-lacZ cassette derived from pAbT 4523 was the most active in transient expression assays (Table 1). To create plasmids to facilitate the formation and identification of recombinant FPV, this BamHI ended cassette was cloned: (1) into the Xba I site in the middle of the FPV thymidine kinase gene (pAbT 2122); (2) into the single BglII site located 960 bp from the end of the 6.8 kb Bam HI J fragment of the FPV genome (pAbT 2300); and (3) in conjunction with a 702 bp DNA fragment containing the vaccinia thymidine kinase gene into the Xba I site of the FPV thymidine kinase gene (pAbT 2124).

Figure 2A:
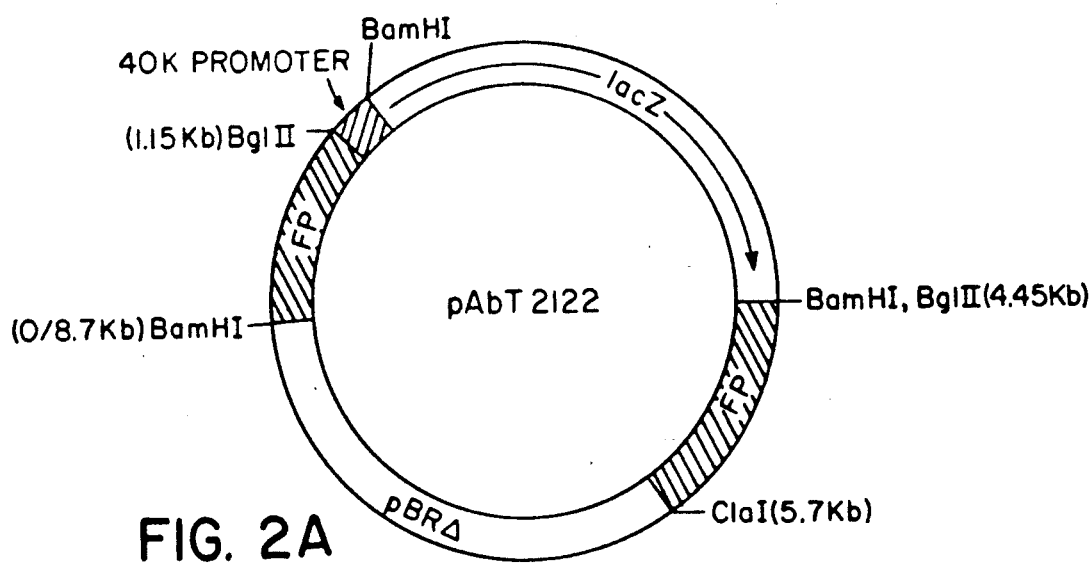
FIG. 2A-C shows plasmids containing the promoter-lacZ cassette derived from pAbT 4523 flanked by FPV DNA sequences to direct insertion into the genome by homologous recombination.
Figure 2B:
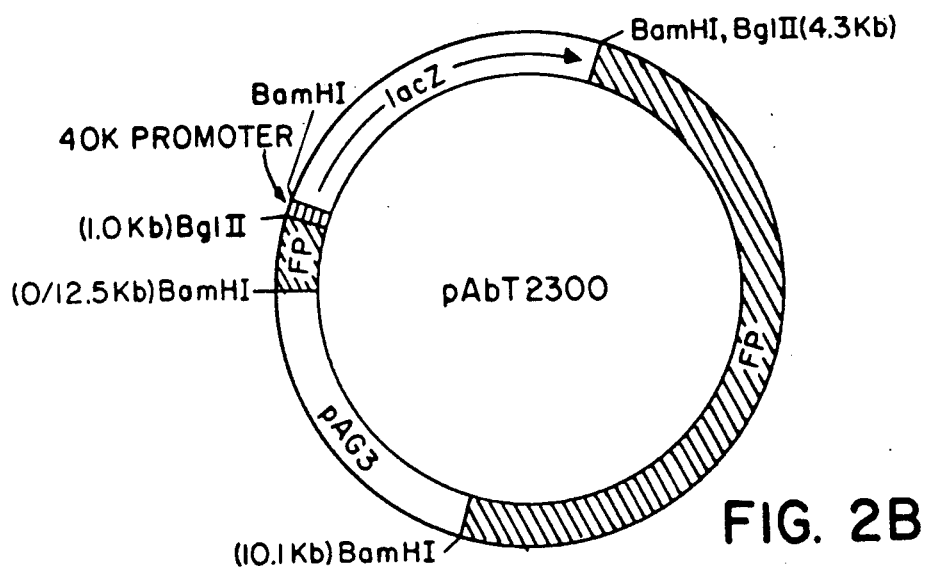
Figure 2C:
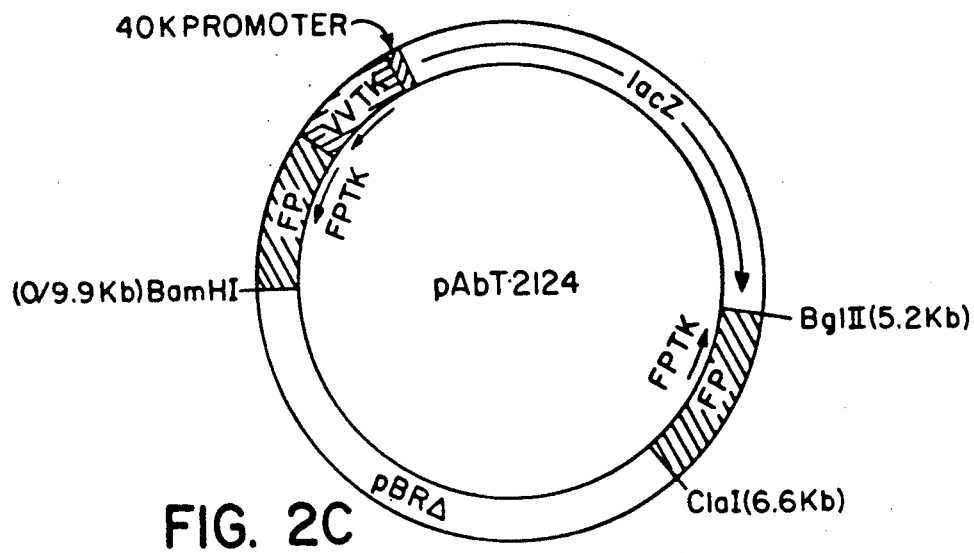
Figure 3A:
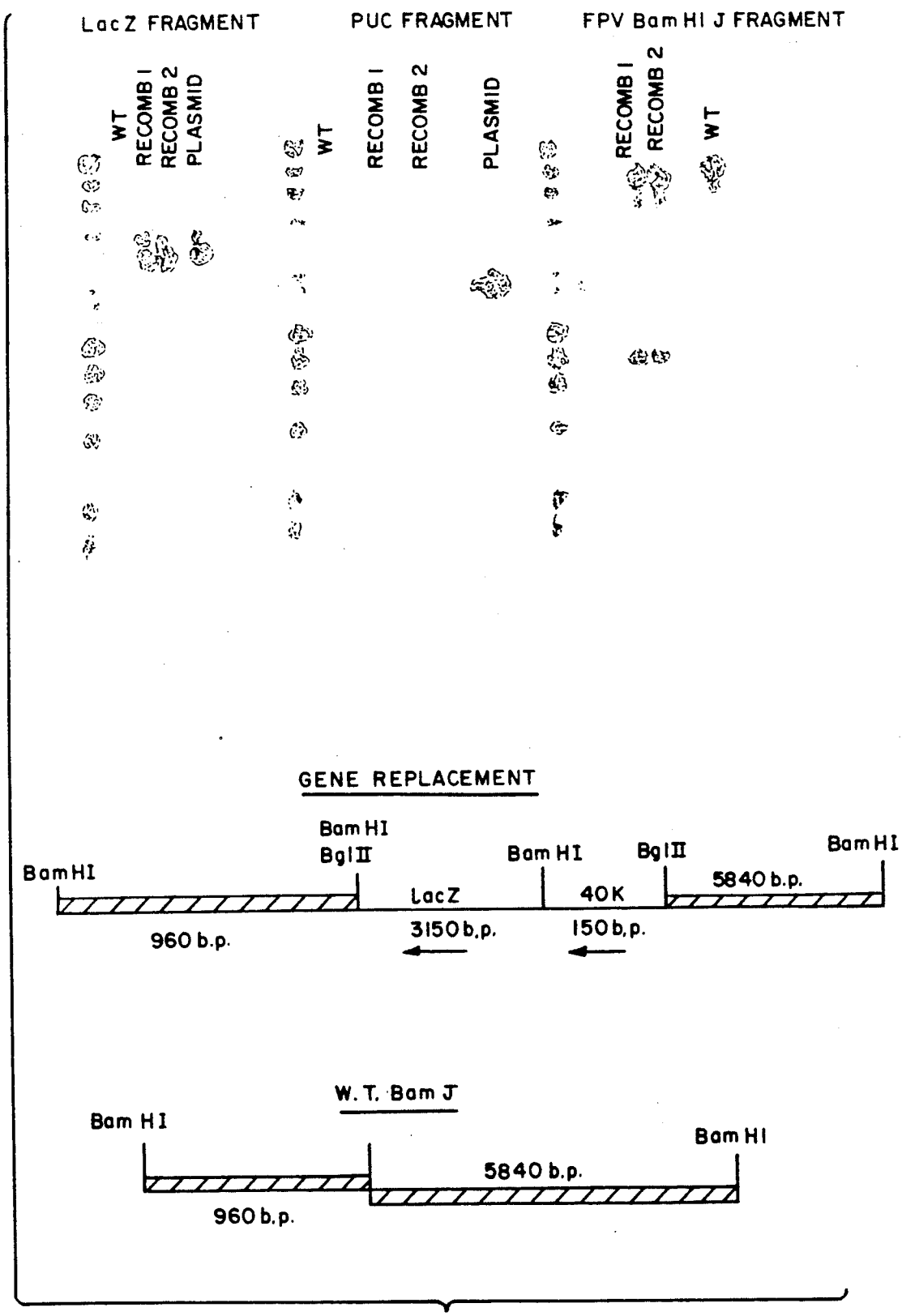
Figure 4A:
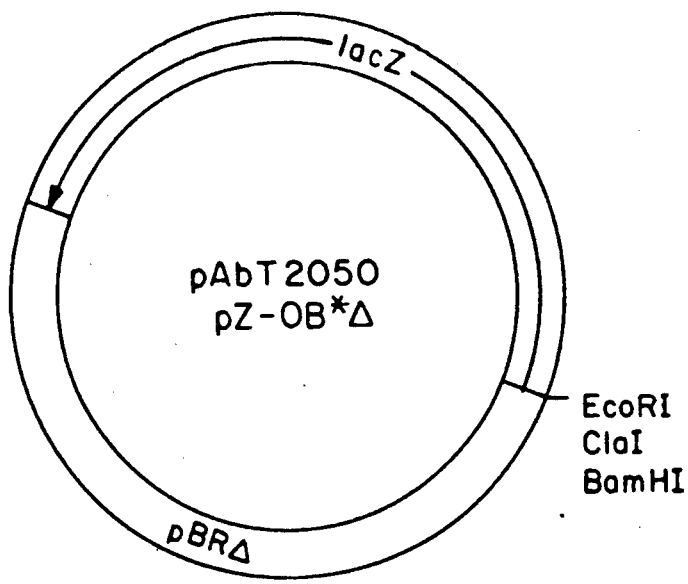
FIG. 4A-D shows the plasmids into which fragments of FPV genome DNA were cloned to identify FPV promoter elements.
Figure 4B:
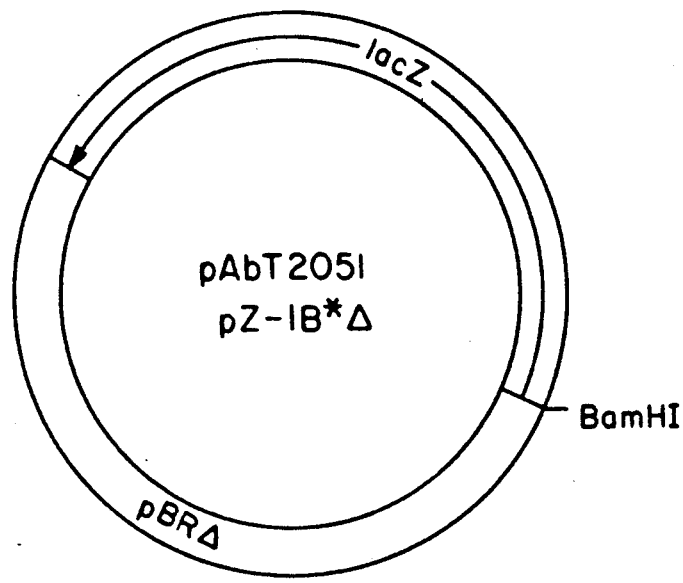
Figure 4C:
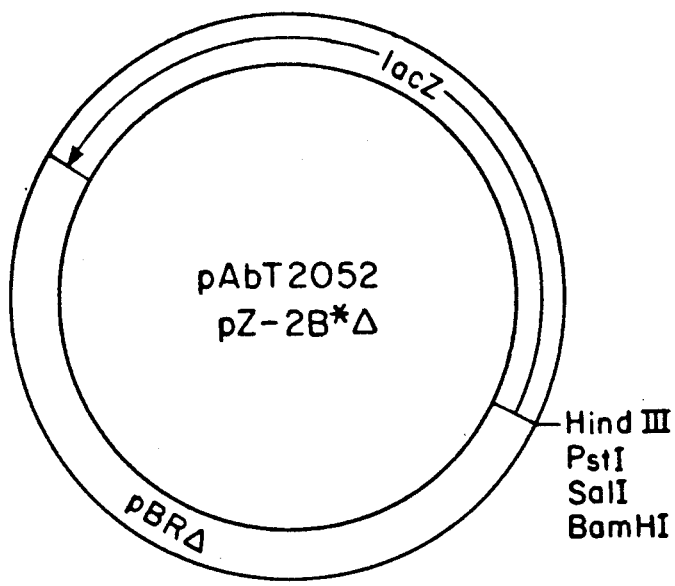
Figure 4D:
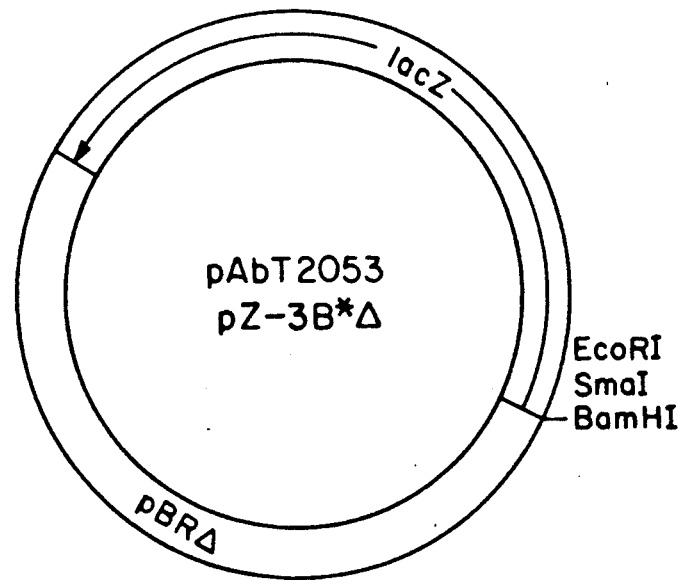

The resulting plasmids which are shown in FIG. 2 contain the promoter-lacZ cassette to allow the detection of recombinant virus, and flanking FPV sequences to direct insertion into the genome by homologous recombination. The FPV thymidine kinase gene was chosen for insertion as it is one of the few which have been identified on the FPV genome. For vaccinia virus it serves as an insertion site which is nonessential for growth in tissue culture (Panicali, D., and E. Paoletti (1982) *Proc. Natl. Acad. Sci USA* 79:4927-4931). The vaccinia virus thymidine kinase gene was included along with the promoter lacZ cassette at this site in pAbT 2124 to complement the loss of the FPV thymioline kimase activity in case this function is required for viral replication. Insertion of the lacZ cassette at the BglII site in the Bam HI J clone was picked at random.

The conditions chosen for the formation of FPV recombinants by homologous recombination were based on those optimized for vaccinia virus and modified based on some knowledge of the growth cycle of FPV in tissue culture cells. For the initial experiment, 20 μg of pAbT 2122 were added to individual monolayers which had been infected with FPV at an moi of 0.1 at 2, 4, 6, 12, and 24 hours post-infection. Viral replication and recombination were allowed to proceed for a total of 72 hours at which time the viral progeny were harvested and the viral titers determined.

The progeny from these experiments initially were examined for the presence of recombinants with a single cell beta-galactosidase assay which allows large numbers of events to be screened. Microscopic examination revealed individual beta-galactosidase expressing cells in monolayers infected with the viral stocks in which pAbT 2122 had been employed in the transfections. No beta-galactosidase expressing cells were detected in uninfected monolayers or in monolayers which had been infected with viral stocks created in the absence of transfected DNA. These results clearly indicated that viral recombinants had been formed.

In order to confirm these results and to provide some measure of the recombination frequency, progeny from each of the viral stocks created in the presence of pAbT 2122 were allowed to form plaques and overlayed with X-gal to detect beta-galactosidase expressing virus. As shown in Table 2, a maximum recombination frequency of 0.03% was obtained by the addition of DNA 4 hours post-infection and the frequency declined when the DNA was added at later times.

TABLE 2
FREQUENCY OF RECOMBINATION BETWEEN FPV AND A PLASMID CONTAINING THE FPV-TK INTERRUPTED BY LACZ

| Time of DNA Addn. | % Recombinants |
| --- | --- |
| 2 hr | .013 |
| 4 hr | .030 |
| 6 hr | .025 |
| 12 hr | .017 |
| 24 hr | .005 |

An average of 140,000 plaques were screened for each time point.

Example 3: Purification of Recombinant FPV and Definition of Insertion Sites The experiments described above have established conditions which allow the formation of FPV recombinants. Insertion of foreign DNA into the FPV genome by homologous recombination can result in either stable gene replacements or unstable gene duplications (Spyropoulos, D.D., B.E. Roberts, D.L. Panicali, and L.K. Cohen (1988) J. Virol. 62:1046-1054). The definition of insertion sites which are nonessential for growth in tissue culture can, therefore, be only ascertained by the creation of homogeneous, stable viral stocks followed by a confirmation of the genomic structure.

To define nonessential insertion sites, plasmids pAbT 2122, 2300, and 2124 were employed in in vivo recombination (IVR) experiments as described above, and the resulting virus allowed to form plaques and overlaid with X-gal to identify recombinants. Two recombinant progeny derived from each of these individual IVRs were picked and replated to assess their purity. This process of picking and replating was repeated for 6 rounds as detailed in Table 3. The progeny derived from IVRs conducted with plasmids pAbT 2300 and 2124 were purified to produce homogeneous, stable stocks of recombinant virus, while those derived from plasmid pAbT 2122 failed to purify.

TABLE 3

PURIFICATION OF RECOMBINANT VIRUS

| | Purification Rounds | | | | | |
|---|---|---|---|---|---|---|
| Plasmid | 1 | 2 | 3 | 4 | 5 | 6 |
| 2300 | .002% | 11% | 53% | 94% | 90% | 100% |
| 2124 | .03% | 7% | 1% | 19% | 100% | 100% |
| 2122 | .002% | 3% | 18% | 0% | — | — |

The % recombinants formed in recombination experiments (Round 1), and their purification in subsequent rounds of plaque purification.

To confirm these phenotypic data, the viral progeny contained within the plaques which demonstrated homogeneity were amplified and used to prepare viral genomic DNA. Viral DNAs were digested with restriction endonucleases, resolved by agarose gel electrophoresis, and subjected to hybridization analysis with the appropriate DNA fragments. The results of an analysis of the recombinants generated with plasmid pAbT 2300 are shown in FIG. 3A. Viral DNA derived from wild type FPV and two recombinant virus were digested with Bam HI and hybridized to: (1) the FPV Bam HI J fragment; (2) the lacZ fragment; and (3) the pUC 18-derived vector sequences. As expected, hybridization of the wild type genomic DNA with the Bam HI J sequences produced a band at 6.8 kb. No hybridization was detected with either the lacZ or vector sequences. Each of the two recombinants produced identical patterns of hybridization with each of the fragments. As predicted for a recombinant FPV formed by a gene replacement event, hybridization with the Bam HI J sequences produced two hybridizing species at approximately 5.8 and 1.0 kb. Hybridization with the lacZ sequences produced a single hybridizing species at 3.2 kb, and no hybridization was detected with the vector DNA. These results confirm the predicted genomic structure shown in FIG. 3A, and define the BglII site in the FPV Bam HI J fragment as nonessential for growth in tissue culture.

FIG. 3B shows a similar analysis conducted on the recombinants formed with plasmid pAbT 2124. The viral DNAs derived from wild type FPV and two recombinants were digested with restriction endonuclease Xba I, and the resulting fragments resolved by agarose gel electrophoresis and hybridized to a 2.4 kb Bam HI-Cla I fragment containing the FPV-TK gene. As expected, hybridization of the wild type genomic DNA produced bands at 3.3 kb, 1.2 kb, and 0.7 kb. As predicted for the recombinants formed by gene replacement events hybridization with the FPV-TK fragment produced three species at 6.4 kb, 1.6 kb, and 1.2 kb. These results confirm the predicted genomic structure shown in FIG. 3B, and indicate that the FPV-TK gene can be used as an insertion site when complemented by the vaccinia virus TK.

Example 4: FPV-Derived Promoter Elements

The promoter used in the identification of the recombinant FPV as well as the two most active promoters detected in the transient expression assays were obtained from vaccinia virus genomic DNA. In order to derive a eukaryotic expression system based entirely upon FPV an attempt was made to define FPV-derived elements as active as the two vaccinia promoters. As shown in FIG. 4, plasmids pZOB*, pZ1B*, pZ2B*, and pZ3B* contain the lacZ gene preceded by a single Bam HI insertion site (Panicali, D.L., A. Grzelecki, and C. Huang (1986) *Gene* 47:193–199). The plasmids differ from each other in that the lacZ gene in pZOB* contains its own translational start codon while the lacZ gene in the other three do not contain start codons but are positioned in each of the three possible reading frames with respect to the Ban HI site. Fragments cloned into all four plasmids can be assayed for their ability to direct transcription of lacZ, producing beta-galactosidase in transient expression assays. This allows the identification of fragments which contain isolated promoter elements or promoters and their associated translational start codons (Panicali, D.L., A. Grzelecki, and C. Huang (1986) *Gene* 47:193–199).

The fragments derived from a total Sau 3AI digest of FPV genomic DNA were cloned into the single Bam HI site in each of the four plasmids in FIG. 4. The average size of the Sau 3AI fragments was approximately 150–200 bp. Initially, the resulting clones were screened for promoter activity in *E. coli* as previous studies have demonstrated the functional cross-reactivity of poxvirus and prokaryotic promoters (data not shown). Plasmid DNA was isolated from those bacterial colonies which expressed beta-galactosidase and tested for authentic promoter activity in the FPV-based transient expression assay.

Table 4 shows the results from a transient expression assay conducted on 16 pools, each containing 5 of the Sau 3AI clones. Clearly, beta-galactosidase activity is detectable in assays conducted with the DNAs present in pool C. To assess the individual contributions to that activity, the individual clones which comprise pool C were separately tested. As seen in Table 5, only four of the five clones composing group C could be revived from frozen stocks, but two of the clones, designated $C_1$ and $C_2$, demonstrated significant promoter activity.

TABLE 4

IDENTIFICATION OF FPV-DERIVED PROMOTERS IN THE FPV-BASED TRANSIENT EXPRESSION ASSAY

| DNA POOL | $A_{420}$ |
|---|---|
| B | .059 |
| C | .128 |
| D | .065 |
| E | .056 |
| F | .053 |
| G | .056 |
| H | .056 |
| I | .063 |
| J | .058 |
| K | .067 |
| L | .057 |
| M | .058 |
| N | .054 |
| P | .063 |
| Q | .067 |
| S | .069 |
| none | .055 |

TABLE 5

FOWLPOX PROMOTER ACTIVITY OF POOL C CLONES

| DNA POOL | $A_{420}$ |
|---|---|
| $C_1$ | .507 |
| $C_2$ | .119 |
| $C_3$ | .071 |
| $C_5$ | .063 |
| none | .057 |

A further characterization of FPV promoters $C_1$ and $C_2$ including a comparison of their strengths with those of the two previously characterized vaccinia virus promoters is shown in Table 6. This set of transient expression assays was conducted in the presence and absence of cytosine arabinoside (araC). As an inhibitor of viral DNA replication, ara C allows the temporal regulation of each of the promoters to be defined. Late promoters such as the 11K vaccinia virus promoter in pAbT 405 are dependent upon DNA replication for expression and are, therefore, essentially inactive in the presence of araC. Early promoters which express prior to DNA replication are relatively unaffected by the inclusion of the ara C. constitutive promoters such as the 40K promoter in pAbT 4523, express both prior to and following DNA replication. These show some diminution of activity in the presence of ara C. The results for the FPV promoters $C_1$ and $C_2$ suggest that they possess some late activity and in fact are constituitive promoters cannot be eliminated from these data. It is significant that the FPV promoter $C_1$ demonstrates activity at least equivalent in strength to the strongest vaccinia virus promoter (pAbT 4523).

TABLE 6

COMPARISON OF FOWLPOX PROMOTERS $C_1$ and $C_2$ WITH VACCINIA PROMOTERS

| DNA | AraC | $A_{420}$ |
|---|---|---|
| pAbT 405 | − | .380 |
| pAbT 405 | + | .034 |
| pAbT 4523 | − | .853 |
| pAbT 4523 | + | .563 |
| $C_1$ | − | 1.656 |
| $C_1$ | + | 1.523 |
| $C_2$ | − | .133 |
| $C_2$ | + | .103 |
| none | − | .019 |
| none | + | .026 |

Each of the two FPV promoters has been sequenced and these results are shown in FIG. 5.

Promoter $C_1$ contains its own translational start codon and is linked to the lacZ by a coding fusion. To allow the use of this promoter with genes which contain their own translational start codons, two modifications have been made which are also shown in FIG. 5. In the first the ATG has been changed to an ATA and in the second a termination codon, TAA has been placed 6 nucleotides downstream from the endogenous translational start. These modifications were achieved through the chemical synthesis of two separate 38 bp Dra I to Bam HI DNA linkers and the replacement by excision and religation of the Dra I to Sau 3AI fragment of the original $C_1$ promoter with these modified sequences. Each of the modified promoters were ligated to a lacZ which contained its own translational start codon, and compared to the original promoter in transient expression assays. As shown in Table 7 both modifications successfully eliminated the translational start while retaining promoter activity.

TABLE 7

ACTIVITY OF MODIFIED $C_1$ FPV PROMOTER IN TRANSIENT EXPRESSION ASSAYS.

| Promoter | $A_{420}$ |
|---|---|
| $C_1$ | .341 |
| 2137 | .616 |
| 2138 | .331 |

Transient expression assays were read after 3.0 hrs of incubation in the presence of ONPG. Plasmid pAbT 2137 contains the ATG to ATA modification, and pAbT 2138 contains the TAA insertion.

Promoter $C_2$ contains no translational signals and is used directedly as cloned.

Example 5: Generalized Fowlpox Expression Vectors

Figure 6A:
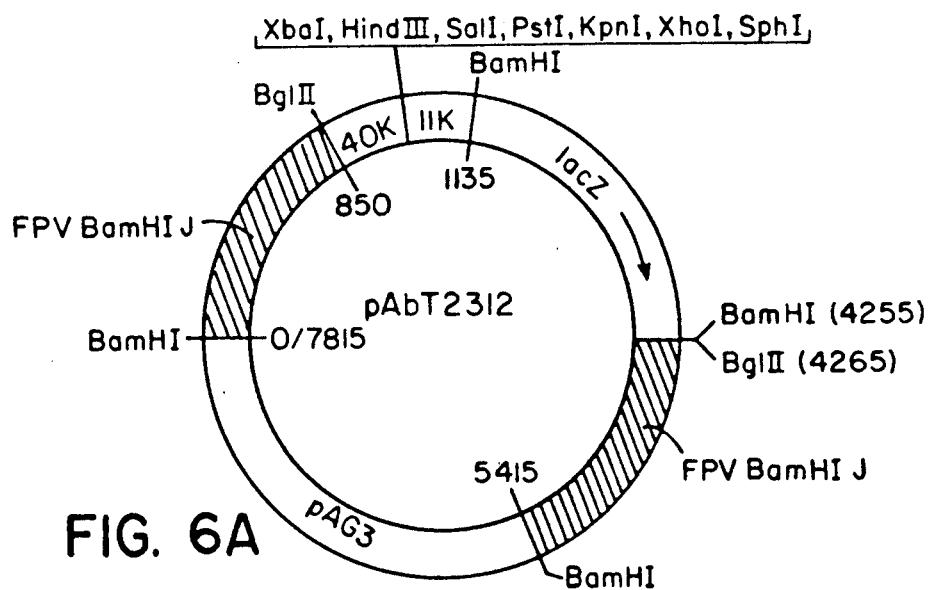
FIG. 6A-C shows generalized plasmids for in vivo recombination with FPV.
Figure 6B:
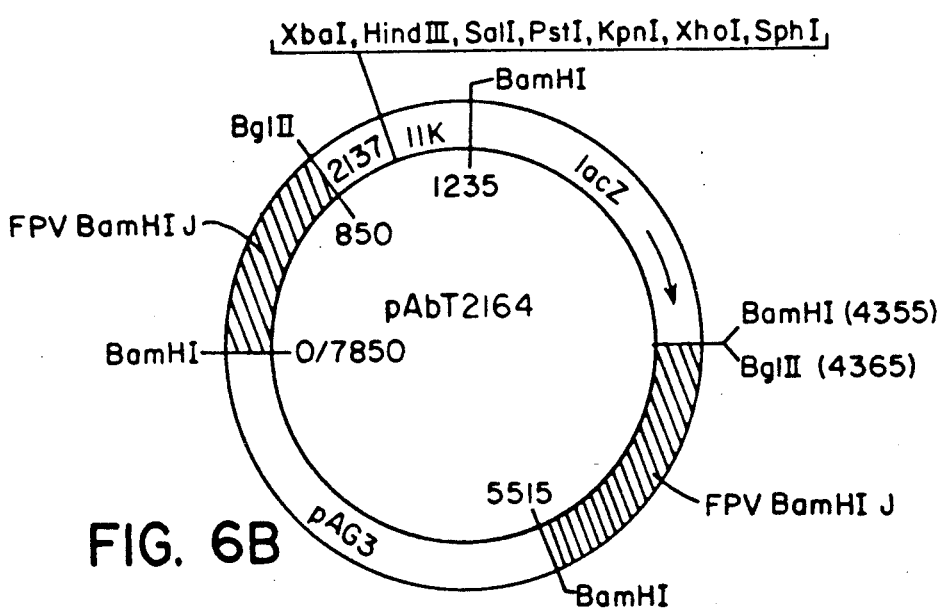
Figure 6C:
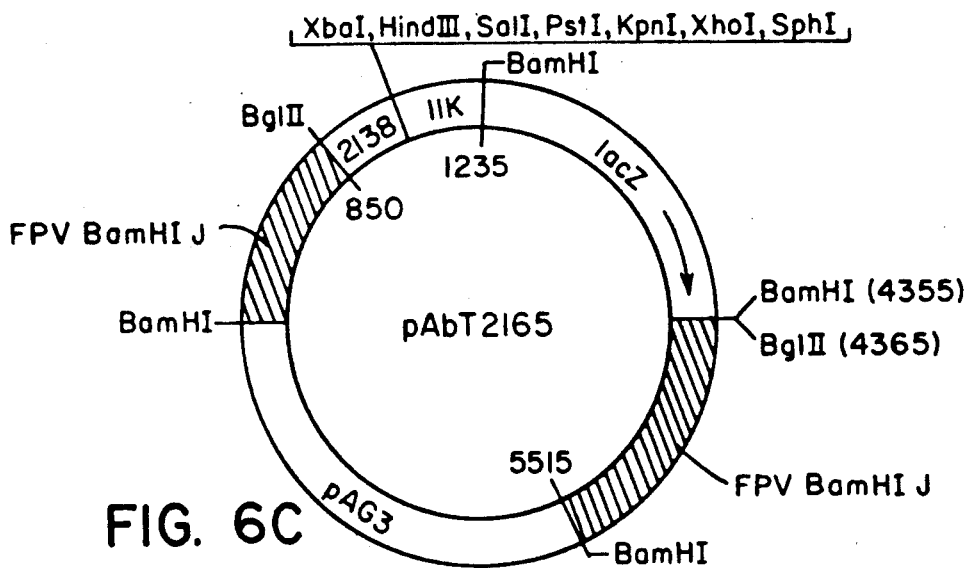

In order to create a system for the expression of any foreign DNA sequences in recombinant FPV, a series of plasmids have been created which are shown in FIG. 6. In addition to DNA sequences which allow selection and replication of these plasmids in bacterial hosts, each plasmid also contains: (1) FPV-derived flanking sequences to direct insertion to a site nonessential for replication in tissue culture; (2) a FPV-active promoter followed by a DNA sequence which contains a multiple cloning site for the insertion of the foreign DNA to be expressed; and (3) an additional FPV-active promoter regulating the synthesis of the lacZ to allow the rapid identification of recombinant virus.

Plasmids pAbT 2312, 2164, and 2165 are designed to facilitate the formation of viral recombinants at the BglII site of the FPV Bam HI J fragments. They differ in whether vaccinia virus or FPV promoter elements are employed. Plasmid pAbt 2312 uses the vaccinia promoters with the stronger promoter derived from plasmid pAbT 4523 (40K promoter) employed to control the synthesis of the foreign gene and the weaker promoter derived from pAbT 405 (11K promoter) to control the synthesis of the lacZ. Plasmids pAbT 2164 and 2165 employ the FPV 2137 and 2138 promoters, respectively, to control the synthesis of the foreign gene and the vaccinia 11K to control the synthesis of the lacZ.

Deposits

The plasmid pAbT 2164 was deposited at the American Type Culture Collection in Rockville, Md. and assigned the accession number ATCC 40485.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A DNA vector for recombination with a fowlpox virus designed to produce a recombination fowlpox virus capable of expressing a foreign DNA sequence, comprising:
   (a) at least one promoter DNA sequence linked to;
   (b) a DNA sequence containing a multiple cloning site for insertion of foreign DNA, the cloning site positioned such that expression of inserted foreign DNA will be controlled by the promoter of element (a); and
   (c) fowlpox DNA sequences flanking the promoter and multiple cloning site at both 5' and 3' ends, the flanking fowlpox sequences being homologous to a region of the fowlpox genome where elements (a) and (b) are to be inserted, wherein the sequences are homologous to the BamHI J fragment, or to a portion thereof sufficient for recombination, flanking the BG1II site.

2. A DNA vector of claim 1, further comprising:
   d. a second promoter linked to a second gene which encodes a marker or indicator for selection of recombinant fowlpox virus, the second promoter and second gene located between the flanking DNA sequences of the DNA vector;
   e. a replicon for vector replication in a prokaryotic host; and
   f. a gene encoding a selectable marker for selection of the vector in a prokaryotic host.

3. A DNA vector of claim 2, wherein the marker gene used for selection of recombinant virus is the lacZ gene.

4. A DNA vector of claim 1, wherein the promoter is a fowlpox promoter.

5. A DNA vector of claim 4, wherein the fowlpox promoter is a C1 promoter having the sequence shown in FIG. 5, a C2 promoter having the sequence shown in FIG. 5, a modified C1 promoter having the sequence shown in FIG. 5, or a portion of said C1, C2, or modified C1 sequence sufficient to function as a promoter.

6. A recombinant fowlpox virus produced by:
   a. inserting one or more foreign DNA sequences into a DNA vector of claim 1, and
   b. allowing the vector containing foreign DNA to undergo recombination with fowlpox virus to produce a recombinant fowlpox virus having inserted into its genome the foreign DNA sequences and a promoter capable of controlling the expression of these foreign DNA sequences.

7. A recombinant fowlpox virus of claim 1, wherein the foreign DNA sequences are those encoding proteins or protein fragments.

8. A recombinant fowlpox virus of claim 6, wherein the promoter is a fowlpox promoter.

9. A recombinant fowlpox virus of claim 8, wherein the fowlpox promoter is a C1 promoter having the sequence shown in FIG. 5, a C2 promoter having the sequence shown in FIG. 5, a modified C1 promoter having the sequence shown in FIG. 5, or a portion of said C1, C2, or modified C1 sequence sufficient to function as a promoter.

10. A DNA vector for insertion of foreign DNA into a fowlpox virus to produce a recombinant fowlpox virus containing the foreign DNA, comprising:
    (a) a promoter linked to;
    (b) a foreign DNA sequence;
    (c) a second promoter linked to a marker gene for selection of recombinant fowlpox virus;
    (d) fowlpox DNA sequences flanking the construct of elements a-c, the flanking fowlpox sequences being homologous to a region of the fowlpox genome where elements a-c are to be inserted, wherein the sequences are homologous to the BamHI J fragment, or to a portion thereof sufficient for recombination, flanking the BglII site;
    (e) a replicon for vector replication in a prokaryotic host cell; and
    (f) a structural gene encoding a marker or indicator for selection of the vector in a prokaryotic host.

11. A DNA vector of claim 10, wherein the foreign DNA sequence is a sequence encoding an immunogenic protein or protein fragment of a pathogen.

12. A DNA vector of claim 10, wherein the marker gene under control of the second promoter is the lacZ gene.

13. A DNA vector of claim 10, wherein the promoter is a fowlpox promoter.

14. A DNA vector of claim 13, wherein the fowlpox promoter is a C1 promoter having the sequence shown in FIG. 5, a C2 promoter having the sequence shown in FIG. 5, a modified C1 promoter having the sequence shown in FIG. 5, or a portion of said C1, C2, or modified C1 sequence sufficient to function as a promoter.

15. The plasmid pAbT2164, ATCC accession number 40485.

16. A DNA vector for recombination with a fowlpox virus designed to produce a recombinant fowlpox virus capable of expressing a foreign DNA sequence, comprising:
    (a) at least one fowlpox viral promoter selected from a C1 promoter having the sequence shown in FIG. 5, a C2 promoter having the sequence shown in FIG. 5, a modified C1 promoter having the sequence shown in FIG. 5, or a portion of said C1, C2, or modified C1 sequence sufficient to function as a promoter, linked to:
    (b) a DNA sequence containing a multiple cloning site for insertion of foreign DNA, the cloning site positioned such that expression of inserted foreign DNA will be controlled by the fowlpox promoter of element (a); and
    (c) fowlpox DNA sequences flanking the promoter and multiple cloning site at both 5' and 3' ends, the flanking fowlpox sequences are homologous to a region of the fowlpox genome where elements a-b are to be inserted, wherein the sequences are homologous to the BamHI J fragment flanking the BglII site of the fowlpox genome, or a portion thereof, sufficient for recombination.

17. A DNA vector for insertion of foreign DNA into a fowlpox virus to produce a recombinant fowlpox virus containing the foreign DNA, comprising:
   (a) a fowlpox viral promoter selected from a C1 promoter having the sequence shown in FIG. 5, a C2 promoter having the sequence shown in FIG. 5, a modified C1 promoter having the sequence shown in FIG. 5, or a portion of said C1, C2, or modified C1 sequence sufficient to function as a promoter, linked to;
   (b) a foreign DNA sequence;
   (c) a second promoter linked to a marker gene for selection of recombinant fowlpox virus;
   (d) fowlpox DNA sequences flanking the construct of elements a-c, or a portion thereof, wherein the flanking fowlpox DNA sequences are homologous to a region of the fowlpox genome where elements a-c are to be inserted, wherein the flanking sequences are homologous the BamHI J fragment flanking the BglII site of the fowlpox genome, or a portion thereof sufficient for recombination;
   (e) a replicon for vector replication in a prokaryotic host cell; and
   (f) a structural gene encoding a marker or indicator for selection of the vector in a prokaryotic host.

18. Recombinant fowlpox virus containing at least one foreign DNA sequence that encodes a polypeptide, the sequence being under the direction of a promoter, wherein the foreign DNA sequence and promoter are inserted into the BglII site of the BamHI J region of the fowlpox viral genome.

19. A recombinant fowlpox virus of claim 18, wherein the promoter is a fowlpox promoter.

20. A recombinant fowlpox virus of claim 19, wherein the fowlpox promoter is a C1 promoter having the sequence shown in FIG. 5, a C2 promoter having the sequence shown in FIG. 5, a modified C1 promoter having the sequence shown in FIG. 5, or a portion of said C1, C2, or modified C1 sequence sufficient to function as a promoter.

* * * * *

UNITED STATES PATENT AND TRADEMARK OFFICE
CERTIFICATE OF CORRECTION

PATENT NO. : 5,093,258

DATED : March 3, 1992

INVENTOR(S) : Lawrence K. Cohen and Dennis L. Panicali

It is certified that error appears in the above-identified patent and that said Letters Patent is hereby corrected as shown below:

Column 1, line 34, replace "dipthenic" with --diphtheric--.

Column 5, lines 6 and 7, replace "coccidiosis salmonella" with --coccidiosis, Salmonella--.

Column 7, line 10, replace "chloranyshenicol" with --chloramphenicol--.
　　　　　line 31, replace "quanine" with --guanine--.
　　　　　line 33, replace "of" with --or--.
　　　　　line 43, replace "closing" with --cloning--.

Column 9, line 16, replace "BluoGalTM" with --BluoGal$^{TM}$--.

Column 11, line 57, replace "ferrioyanide" with --ferricyanide--.

Column 12, line 16, replace "meroaptoethanol" with --mercaptoethanol--.

Column 13, line 40, replace "beta-galac-tosidase" with --beta-galactosidase--.

Column 14, lines 30-31, replace "thymio-line kimase" with --thymidine kinase--

Column 16, line 45, replace "Ban HI" with --Bam HI--.

Column 17, line 50, replace "constitutive" with --Constitutive--.

UNITED STATES PATENT AND TRADEMARK OFFICE
CERTIFICATE OF CORRECTION

PATENT NO. : 5,093,258

DATED : March 3, 1992

INVENTOR(S) : Lawrence K. Cohen, et. al.

It is certified that error appears in the above-indentified patent and that said Letters Patent is hereby corrected as shown below:

Claim 1, line 18, replace "BG lII" with --BglII--.

Signed and Sealed this

Nineteenth Day of October, 1993

Attest:

BRUCE LEHMAN

Attesting Officer     Commissioner of Patents and Trademarks

UNITED STATES PATENT AND TRADEMARK OFFICE
CERTIFICATE OF CORRECTION

PATENT NO. : 5,093,258

DATED : March 3, 1992

INVENTOR(S) : Lawrence K. Cohen and Dennis L. Panicali

It is certified that error appears in the above-identified patent and that said Letters Patent is hereby corrected as shown below:

Column 1, line 54, replace "Standasr" with --Standards--.
Column 1, line 57, replace "innoculation" with --inoculation--.
Column 2, line 55, replace "erradication" with --eradication--.
Column 2, line 60, replace "innoculation" with --inoculation--.
Column 3, line 65, replace "is" with --are--.
Column 4, line 67, replace ";" with --:--.
Column 5, line 7, replace "auereus" with --aureus--.
Column 6, line 8, replace "a and b," with --a. and b.,--.
Column 6, line 43, replace "a" with --a.--.
Column 6, line 43, replace "b" with --b.--.
Column 7, line 51, replace "a-d;" with --a.-d.;--.
Column 11, line 49, replace "media" with --medium--.
Column 12, line 7, replace "Tris-Cl" with --Tris-Hcl--.
Column 12, line 26, replace "Tris-cl" with --Tris-Hcl--.
Column 14, line 27, replace "Sci USA" with --Sci. USA--.
Column 17, line 56, replace "constituitive" with --constitutive--.
Column 18, line 67, replace "pAbt" with --pAbT--.

Column 19, Claim 2, line 42, replace "d." with --(d)--.
Column 19, Claim 2, line 47, replace "e." with --(e)--.

UNITED STATES PATENT AND TRADEMARK OFFICE
CERTIFICATE OF CORRECTION

PATENT NO. : 5,093,258

DATED : 03/03/92

INVENTOR(S) : Lawrence K. Cohen and Dennis L. Panicali

It is certified that error appears in the above-indentified patent and that said Letters Patent is hereby corrected as shown below:

Column 19, Claim 2, line 9, replace "f." with --(f)--.
           Claim 6, line 2, replace "a." with --(a)--.
           Claim 6, line 4, replace "b." with --(b)--.

Signed and Sealed this

Fourth Day of January, 1994

Attest:

BRUCE LEHMAN

Attesting Officer     Commissioner of Patents and Trademarks